(12) United States Patent
Bachman et al.

(10) Patent No.: US 6,247,929 B1
(45) Date of Patent: Jun. 19, 2001

(54) ORAL IRRIGATOR HANDLE ASSEMBLY HAVING A PRESSURE CONTROL VALVE AND STOP VALVE ASSEMBLY

(75) Inventors: Timothy A. Bachman; Gary Ashurst; Floyd J. Binder, all of Fort Collins, CO (US)

(73) Assignee: Teledyne Industries, Inc., Fort Collins, CO (US)

( * ) Notice: Subject to any disclaimer, the term of this patent is extended or adjusted under 35 U.S.C. 154(b) by 0 days.

(21) Appl. No.: 09/217,972

(22) Filed: Dec. 18, 1998

(51) Int. Cl.$^7$ .................................................. A61G 17/02
(52) U.S. Cl. .................................................. 433/80; 433/84
(58) Field of Search .................................. 433/80, 81, 82, 433/83, 84, 85, 86, 87, 88

(56) References Cited

U.S. PATENT DOCUMENTS

| | | |
|---|---|---|
| 3,227,158 | 1/1966 | Mattingly . |
| 3,522,801 | 8/1970 | Robinson . |
| 3,547,110 | 12/1970 | Balamuth . |
| 3,636,947 | 1/1972 | Balamuth . |
| 3,651,576 | 3/1972 | Massa . |
| 3,809,977 | 5/1974 | Balamuth et al. . |
| 4,060,870 | 12/1977 | Cannarella . |
| 4,075,761 | 2/1978 | Behne et al. . |
| 4,108,178 | 8/1978 | Betush . |
| 4,144,646 | 3/1979 | Takemoto et al. . |
| 4,182,038 | 1/1980 | Fleer . |
| 4,215,476 | 8/1980 | Armstrong . |
| 4,219,618 | 8/1980 | Leonard . |
| 4,227,878 | 10/1980 | Löhn . |
| 4,229,634 | 10/1980 | Hickman et al. . |
| 4,236,889 | 12/1980 | Wright . |
| 4,249,899 | 2/1981 | Davis . |
| 4,266,934 | 5/1981 | Pernot . |
| 4,276,023 | 6/1981 | Phillips et al. . |
| 4,302,186 | 11/1981 | Cammack et al. . |
| 4,331,422 | 5/1982 | Heyman . |
| 4,340,365 | 7/1982 | Pisanu . |
| 4,340,368 | 7/1982 | Lococo . |
| 4,363,626 | 12/1982 | Schmidt et al. . |
| 4,365,376 | 12/1982 | Oda et al. . |
| 4,382,786 | 5/1983 | Löhn . |
| 4,412,823 | 11/1983 | Sakai et al. . |
| 4,517,962 | 5/1985 | Heckele . |
| 4,531,912 | 7/1985 | Schuss et al. . |
| 4,531,913 | 7/1985 | Taguchi . |
| 4,602,906 | 7/1986 | Grünenfelder . |
| 4,619,612 | 10/1986 | Weber et al. . |
| 4,629,425 | 12/1986 | Detsch . |
| 4,648,838 | 3/1987 | Schlachter . |
| 4,655,198 | 4/1987 | Hommann . |
| 4,669,453 | 6/1987 | Atkinson et al. . |
| 4,672,953 | 6/1987 | DiVito . |

(List continued on next page.)

OTHER PUBLICATIONS

WOOG® Products at a Glance Brochure, Home Dental Care System, Woog Orajet, at least as early as Dec. 18, 1998.

*Primary Examiner*—Nicholas D. Lucchesi
(74) *Attorney, Agent, or Firm*—Holland & Hart LLP

(57) ABSTRACT

A hand piece assembly for an oral irrigator having a pressure control valve assembly, a stop valve, and a housing. The pressure control valve assembly has a valve body having an intermediate section having a substantially cylindrical bore therethrough. A valve gate having a cylindrical portion with an orifice bored therethrough has a control arm coupled to a guide portion for rotation within the valve body. A slide control is positioned on the housing and is coupled to guide portion of the valve gate, so that as the slide control moves linearly along a portion of the housing, the cylindrical portion of the valve gate correspondingly rotates within the bore of the valve body to adjust the pressure or flow rate of the fluid passing through the pressure control valve assembly.

22 Claims, 15 Drawing Sheets

U.S. PATENT DOCUMENTS

| | | |
|---|---|---|
| 4,787,847 | 11/1988 | Martin et al. . |
| 4,803,974 | 2/1989 | Powell . |
| 4,804,364 | 2/1989 | Dieras et al. . |
| 4,818,229 | 4/1989 | Vasile . |
| 4,820,152 | 4/1989 | Warrin et al. . |
| 4,826,431 | 5/1989 | Fujimura et al. . |
| 4,832,683 | 5/1989 | Idemoto et al. . |
| 4,854,869 | 8/1989 | Lawhorn . |
| 4,886,452 | 12/1989 | Löhn . |
| 4,902,225 | 2/1990 | Löhn . |
| 4,903,687 | 2/1990 | Lih-Sheng . |
| 4,906,187 | 3/1990 | Amandera . |
| 4,928,675 | 5/1990 | Thornton . |
| 4,950,159 | 8/1990 | Hansen . |
| 4,961,698 | 10/1990 | Vlock . |
| 4,973,247 | 11/1990 | Varnes et al. . |
| 4,975,054 | 12/1990 | Esrock . |
| 4,979,503 | 12/1990 | Chernack . |
| 4,989,590 | 2/1991 | Baum et al. . |
| 4,998,880 | 3/1991 | Nerli . |
| 5,013,241 | 5/1991 | von Gutfeld et al. . |
| 5,027,798 | 7/1991 | Primiano . |
| 5,033,961 | 7/1991 | Kankler et al. . |
| 5,082,443 | 1/1992 | Löhn . |
| 5,086,756 | 2/1992 | Powell . |
| 5,095,893 | 3/1992 | Rawden, Jr. . |
| 5,125,835 | 6/1992 | Young . |
| 5,142,723 | 9/1992 | Lustig et al. . |
| 5,199,871 | 4/1993 | Young . |
| 5,204,004 | 4/1993 | Johnston et al. . |
| 5,218,956 | 6/1993 | Handler et al. . |
| 5,220,914 | 6/1993 | Thompson . |
| 5,246,367 | 9/1993 | Ito et al. . |
| 5,252,064 | 10/1993 | Baum et al. . |
| 5,281,137 | 1/1994 | Jousson . |
| 5,286,201 | 2/1994 | Yu . |
| 5,321,865 | 6/1994 | Kaeser . |
| 5,344,317 | 9/1994 | Pächer et al. . |
| 5,378,149 | 1/1995 | Stropko . |
| 5,399,089 | 3/1995 | Eichman et al. . |
| 5,456,672 | 10/1995 | Diederich et al. . |
| 5,468,148 | 11/1995 | Ricks . |
| 5,470,305 | 11/1995 | Arnett et al. . |
| 5,474,450 | 12/1995 | Chronister . |
| 5,484,281 | 1/1996 | Renow et al. . |
| 5,547,374 | 8/1996 | Coleman . |
| 5,554,025 | 9/1996 | Kinsel . |
| 5,616,028 | 4/1997 | Häfele et al. . |
| 5,636,987 | 6/1997 | Serfaty . |
| 5,640,735 | 6/1997 | Manning . |
| 5,697,784 | 12/1997 | Häfele et al. . |
| 5,709,545 | 1/1998 | Johnston et al. . |

ORAL IRRIGATOR HANDLE ASSEMBLY HAVING A PRESSURE CONTROL VALVE AND STOP VALVE ASSEMBLY

INCORPORATION BY REFERENCE

This application is related to co-pending U.S. patent application entitled "Oral Irrigator Housing," Ser.No. 09/217,973, filed concurrently herewith, and assigned to the assignee of this application, the disclosure of which is hereby incorporated by reference in its entirety. The following U.S. patents, which are assigned to the assignee of the present application, are also incorporated herein by reference in their entirety: U.S. Pat. No. 4,989,590, filed Jun. 21, 1990, to John Baum, et al., entitled "Irrigation Appliance"; U.S. Pat. No. 4,302,186, filed Nov. 23, 1979, by Michael Cammack, entitled "Oral Hygiene Appliance"; U.S. Pat. No. 4,229,634, filed Feb. 21, 1978, by Clarence Hickman, et al., entitled "Insulated Switch Arrangement for Electric Motor"; and U.S. Pat. No. 5,399,089, filed Aug. 11, 1993, by Kim Eichman, et al., entitled "Oral Hygiene Appliance".

FIELD OF THE INVENTION

This invention relates to oral irrigator handles and valves, and more particularly relates to oral irrigator handles having pressure control valves and a momentary stop or pause control.

BACKGROUND OF THE INVENTION

Oral irrigators are very popular dental hygiene devices used for maintaining healthy gums by delivering pulses or streams of pressurized fluid through a handle to a user's teeth and gums. While some oral hygiene devices include electronic motors or other active elements in the handle, there is a need for an oral irrigator which supplies pressurized fluid to the teeth and gums of a user without having any active electronic elements within the handle of the device. One such passive oral irrigator is shown in U.S. Pat. No. 5,399,089, filed Aug. 11, 1993 by Kim Eichman, et al., entitled "Oral Hygiene Appliance" which is assigned to the assignee of the present application and which is hereby incorporated by reference in its entirety.

In the design of an oral irrigator, one consideration involves the control of the flow rate of the water or fluid through the handle of the oral irrigator. In U.S. Pat. No. 5,399,089, for instance, a push button is biased outwardly by a spring, and when depressed, the push button moves the end of a rod inwardly to close an interior passage of a fluid flow conduit and thus cuts off fluid flow.

Rotary pressure controls used to control the pressure within an oral irrigator are typically located on the housing of the oral irrigator or the handle. When positioned on the housing, the rotary pressure controls can be inconvenient to use because the user has to reach to the housing of the oral irrigator in order to manipulate the dial. When the rotary pressure controls are located on the handle, the control is difficult to use because the user may have to move inconveniently his or her hand about or off of the handle in order to manipulate the rotary pressure control.

What is needed is an oral irrigator handle assembly having a pressure control valve and a stop valve, where the pressure control valve has a slide or linear control with linear travel to provide the user with visual and or audible feedback as to the pressure control setting of the slide control.

SUMMARY OF THE INVENTION

The oral irrigator hand piece assembly of the present invention, including the pressure control and stop valves, was developed with the shortcomings of conventional oral irrigators in mind.

In light of the above, and according to a broad aspect of the invention, a pressure control valve for a handle of an oral irrigation device is disclosed herein. The pressure control valve assembly includes a linearly actuated slide control positioned on the handle which is coupled to a rotary valve inside the handle along the fluid flow path. The linear motion of the slide control is converted into a proportional amount of rotational movement of the rotary valve within the valve body to control the fluid flow pressure. In particular, as the slide control is moved linearly along its actuating length, the slide control causes the rotary valve to rotate within the valve body and increases or decreases the effective diameter of the fluid flow path through the valve, thereby regulating the fluid flow pressure through the hand piece assembly. The pressure control valve assembly permits the user of the oral irrigator to continuously regulate fluid flow pressure through the hand piece assembly between a low pressure and a high pressure value of the fluid flowing to the user's teeth or gums.

In one embodiment of the present invention, the pressure control valve has a valve body, a valve member, and a slide control. The valve body has an input section defining an input fluid flow path, an intermediate section having a substantially cylindrical bore therethrough, and a output section defining an output fluid flow path, where the input fluid flow path is fluidly coupled to the output fluid flow path through the bore. The valve member has an orifice bored therethrough and is positioned in the cylindrical bore and is rotatable therein. The slide control is positioned on the housing of the handle of the oral irrigator, the slide control being coupled to the valve member so that as the slide control moves linearly along a portion of the housing, the valve member rotates within the bore of the valve body. As the slide control moves linearly along a portion of the housing, the valve member rotates within the bore of the valve body between a first position where the orifice is substantially aligned between the input fluid flow path and the output fluid flow path, to a second position where the orifice is substantially mis-aligned between the input fluid flow path and the output fluid flow path. In this manner, the effective diameter for fluid flow between the input fluid flow path and the output fluid flow path is altered which alters the pressure at which fluid is delivered to the output fluid flow path.

According to another broad aspect of the invention, a pressure control valve for a handle of an oral irrigation device is disclosed having a valve body, a valve gate, and a slide control. The valve body has an input section defining an input fluid flow path, an intermediate section having a substantially cylindrical bore therethrough, and a output section defining an output fluid flow path, where the input fluid flow path fluidly coupled to the output fluid flow path through the bore. The valve gate has a cylindrical portion having an orifice bored therethrough, a guide portion, and a control arm having a first end coupled to the cylindrical portion and a second end coupled to the guide portion. The slide control is coupled to guide portion of the valve gate, so that as the slide control moves linearly, the cylindrical portion of the valve gate correspondingly rotates within the bore of the valve body, thereby altering the pressure of fluid flow through the oral irrigation device.

The cylindrical portion of the valve gate has a pair of recessed annular channels about the orifice for receiving a pair of 0-rings. The cylindrical portion is rotatable between a first orientation where the orifice is substantially aligned between the input fluid flow path and the output fluid flow path, to a second orientation where the orifice is substantially mis-aligned between the input fluid flow path and the output fluid flow path.

The slide control has pair of upwardly extending yokes with a gap formed therebetween, and the guide portion is positioned in the gap portion. The interior surface of the slide control has a plurality of raised indices adapted to contact a protrusion on the handle as the slide control is linearly moved along the housing, which provides the user with tactile and audible feedback.

According to another broad aspect of the invention, a handle assembly for an oral irrigator is disclosed having a housing and a pressure control valve having a slide control for adjusting the pressure of the fluid flow therein. The handle assembly can also include a stop valve assembly for momentarily stopping the flow of fluid through the handle assembly. The stop valve assembly includes a plunger having a generally elongated body and plurality of recessed annular rings along the body, a plurality of O-rings adapted to each be placed within one of the annular rings, and a stop valve body having an input chamber defining an input fluid flow path, an intermediate chamber having a first interior diameter and a second interior diameter, and an output chamber defining an output fluid flow path. The input fluid flow path is fluidly coupled to the output fluid flow path through the intermediate chamber, so that as the plunger is depressed within the stop valve body, the plunger blocks the fluid flow with the intermediate chamber. The stop valve assembly further includes a spring biasing the plunger in a normally open within the stop valve body.

A more complete appreciation of the present invention and its scope can be obtained from understanding the accompanying drawings, which are briefly summarized below, the following detailed description of the presently preferred embodiments of the invention, and the appended claims.

DETAILED DESCRIPTION OF THE PREFERRED EMBODIMENT

Figure 1:
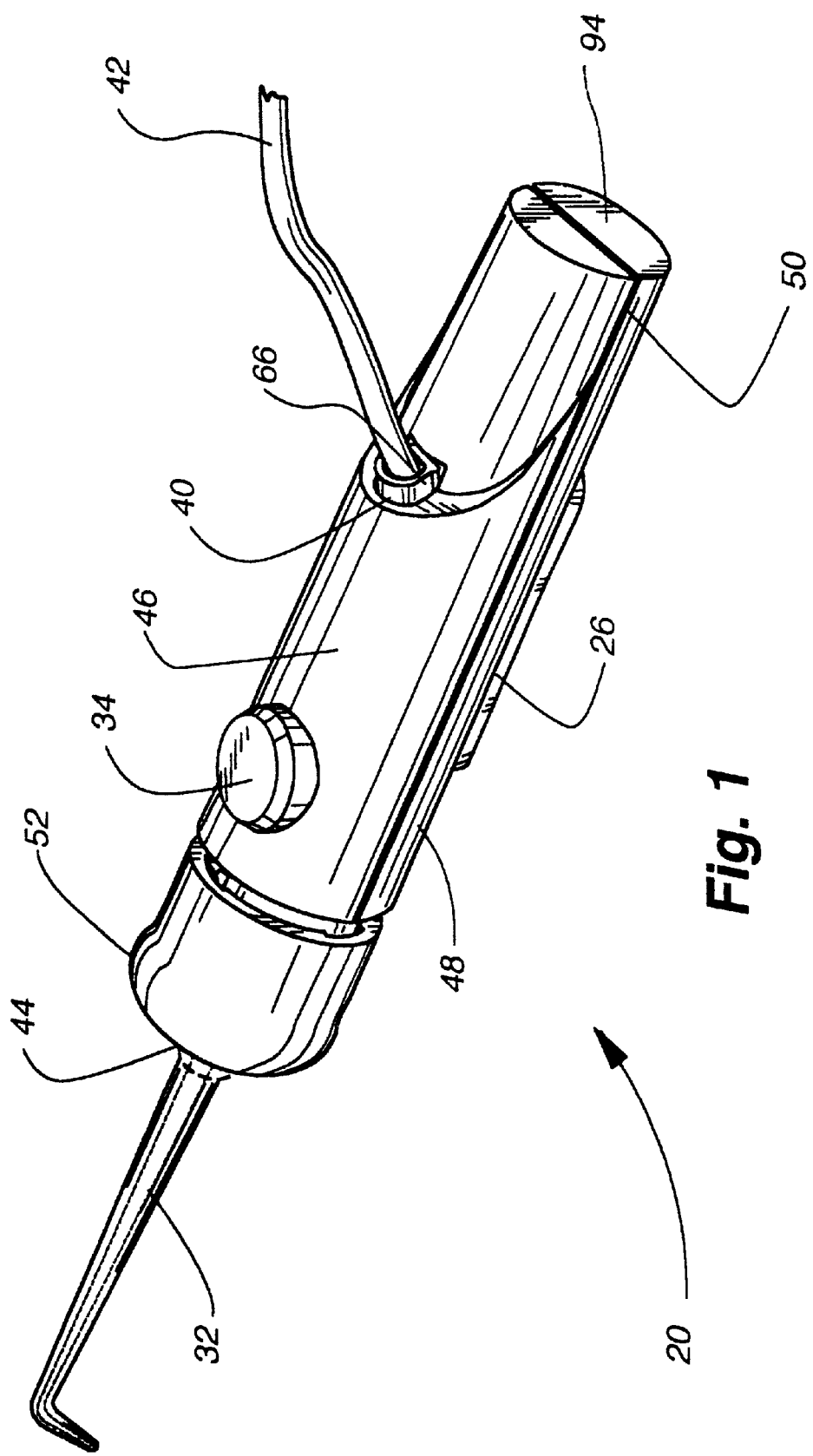
FIG. 1 is a perspective view of the oral irrigator hand piece in accordance with one embodiment of the present invention.

In accordance with the present invention, a hand piece assembly 20 for an oral irrigator is provided having a stop valve assembly 22 and a pressure control valve assembly 24. The stop valve assembly 22 permits the user of the hand piece to momentarily stop or pause the fluid flow through the hand piece of the oral irrigator, as will be described in greater detail below. The pressure control valve assembly 24 permits the user of the oral irrigator to continuously regulate fluid flow pressure through the hand piece assembly between a low pressure and a high pressure value of the fluid flowing to the user's teeth or gums.

More specifically, the pressure control valve assembly 24 includes a linearly actuated slide control 26 positioned on the handle which is coupled to a rotary valve 28 inside the handle along the flow path. The linear motion of the slide control 26 is converted into a proportional amount of rotational movement of the rotary valve 28 within the pressure control valve body 30 to control the fluid flow pressure. In particular, as the slide control 26 is moved linearly along its actuating length, the slide control 26 causes the rotary valve 28 to rotate within the valve body 30 and increases or decreases the effective diameter of the fluid flow path through the valve, thereby regulating the fluid flow pressure through the hand piece assembly 20. As used herein, the term "effective diameter" means the cross-sectional area of the flow path as characterized by a longest cross-sectional dimension.

The stop valve assembly 22 permits the user to temporarily stop or pause the fluid flow out from the jet tip 32 by depressing a push button 34 of the stop valve assembly.

When the push button 34 is released, the fluid pressure delivered through the hand piece assembly 20 increases to the pressure previously established by position of the slide control 26.

Referring now specifically to FIG. 1 and in accordance with the present invention, the hand piece assembly 20 of an oral irrigator is coupled at its fluid receiving input 40 to a tube 42 of the oral irrigator (not shown) which delivers fluid under a substantially constant pressure from the oral irrigator to the hand piece assembly 20. The hand piece assembly is coupled at its fluid delivering output 44 to the nozzle or jet tip 32 which delivers fluid to the user's teeth or gums.

The hand piece has an upper handle member 46 and a lower handle member 48 attached together along a longitudinal half-line 50. The slide control 26 is provided on the hand piece for adjustably controlling the pressure of the fluid delivered, while the push button control 34 is provided on the hand piece for momentarily stopping or pausing fluid flow through the hand piece when the push button 34 is depressed. A knob 52 and collet 54 assembly is also provided on the hand piece to permit the user to insert and remove different jet tips 32 to the hand piece assembly.

Figure 2:
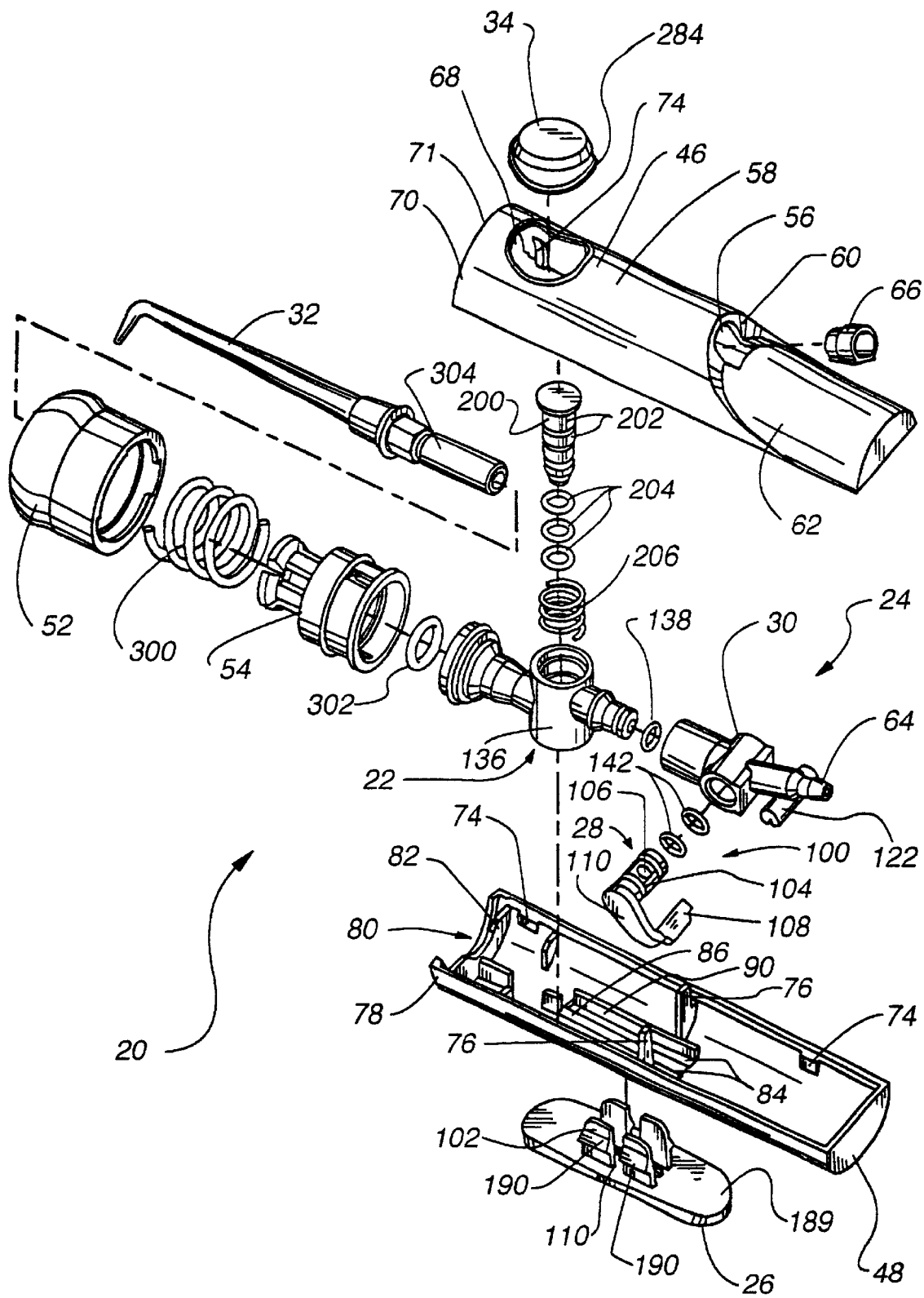
FIG. 2 is an exploded view of the hand piece assembly showing the stop valve assembly and the pressure control valve assembly in accordance with one embodiment of the present invention.

The upper handle member 46 defines an aperture 56 between the exterior portion 58 of the upper handle and along a shelf portion 60 formed between the exterior portion 58 and a contoured offset portion 62, as shown in FIG. 2. This aperture 56 defines an inlet port 40 through which the hose 42 of the oral irrigator is coupled to an input tip portion 64 of the pressure control assembly 24. A hose grommet 66 can be used to secure the hose 42 within the aperture 56 of the upper handle member. The upper handle member 46 also has an aperture 68 adapted to receive the push button 34. At its distal end 70, the upper handle member defines a semicircular aperture 71 and has an annular tab 72 (FIG. 3) therethrough for securably receiving the collet 54 between the upper and lower handle members.

The lower handle member 48 is elongated and generally semicircular and hollow within. The structure of the lower handle member generally serves to support the pressure and stop valve assemblies 24, 22 and the collet 54, and to facilitate attachment of the two handle members together to form the handle. A set of interlocking tabs 74 are provided on the upper and lower handle members which assist in securing the upper and lower handle members together. A pair of upwardly extending braces 76 are provided to support and position the pressure control valve assembly 24 within the hand piece. The lower handle member 48 has at its distal end 78 a circular aperture 80 and an annular ridge 82 which also forms a bearing surface upon which the collet 54 can be secured.

Figure 3:
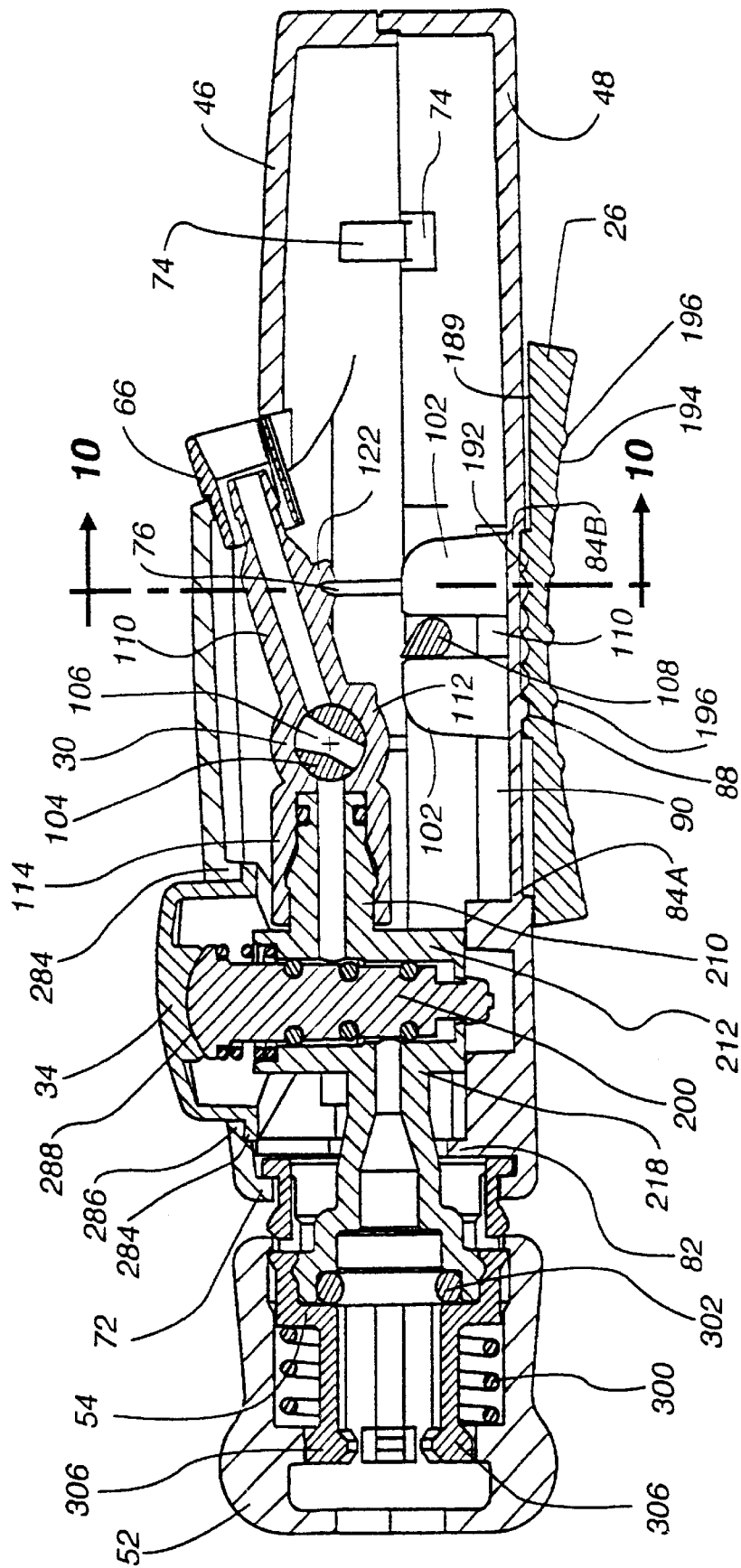
FIG. 3 illustrates a sectional view of the hand piece assembly of one embodiment of the present invention with the pressure control valve in the lowest pressure position.
Figure 16:
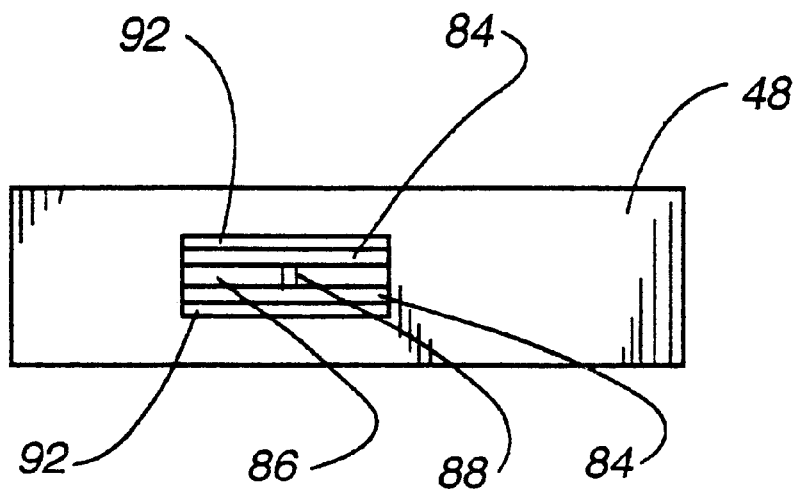
FIG. 16 illustrates a top view of the lower handle portion of the hand piece assembly in accordance of one embodiment of the present invention.

The lower handle member 48 also defines a linear actuating distance, shown for example as the distance between 84A to 84B in FIG. 3, upon which the slide control 26 travels. The lower handle member has a pair of rectangular slots or apertures 84 therethrough which receive a portion of the slide control 26, and a pair of upwardly extending braces 76 for supporting and engaging a portion of the pressure control valve body 30. Between the laterally extending slots 84, a rectangularly spaced bridge portion 86 is provided having a protrusion 88 about its midpoint on the exterior of the lower handle member 48 (see FIG. 16).

A raised guide 90 is provided within the interior of the lower handle member 48 for engagement with a portion of the slide control 26 about the outer side of each of the rectangular slots 84 in the lower handle member. A set of slightly raised, smooth surface guides 92 (FIG. 16) can also be provided along the exterior surface of the lower handle member 26 so to reduce the friction between the slide control 26 and the lower handle member as the slide control is moved along the lower handle member.

The proximate ends 94 of the upper and lower handle member can be shaped to from an asymmetrical profile (Fig. 1) positionable within an aperture formed in the base of an oral irrigator. As described in co-pending U.S. patent application entitled "Oral Irrigator Housing," Ser. No. 09/217,973, referenced above, an aperture in the base of the oral irrigator can be adapted to receive and position the hand piece in a particular orientation with respect to the base of the oral irrigator.

Referring to FIG. 2, the hand piece assembly 20 of one embodiment of the present invention is shown having a pressure control valve 24 assembly and a stop valve assembly 22. A fluid flow path through the hand piece assembly is formed from the hose 42 of the oral irrigator into the input end 64 of the pressure control valve assembly 24, through the stop valve assembly 22, and out through the jet tip 32. The components of the hand piece assembly 20 along the fluid flow path will now be described.

The pressure control valve assembly 24, as shown in FIGS. 2, 3, 5–7, includes a pressure control valve body 30 having multiple chambers, a rotatable valve member such as a valve gate 100, and the slide control 26 having upwardly extending yokes 102 for controlling the rotation of the valve gate 100 within the pressure control valve body. The rotatable valve gate 100 has a cylindrical portion 104 having an orifice 106 bored therethrough and positioned in-line with the fluid flow path, a guide portion 108, and a control arm 110 integral therewith attaching the cylindrical portion 104 to the guide portion 108. The guide portion 108 rests in a slot or cradle 110 formed between the opposing pairs of yokes 102 of the slide control 26, so that as the user linearly moves the slide control, the yokes 102 impart a force on the guide portion 108 which rotates the cylindrical portion 104 within the valve body 30.

Figure 5:
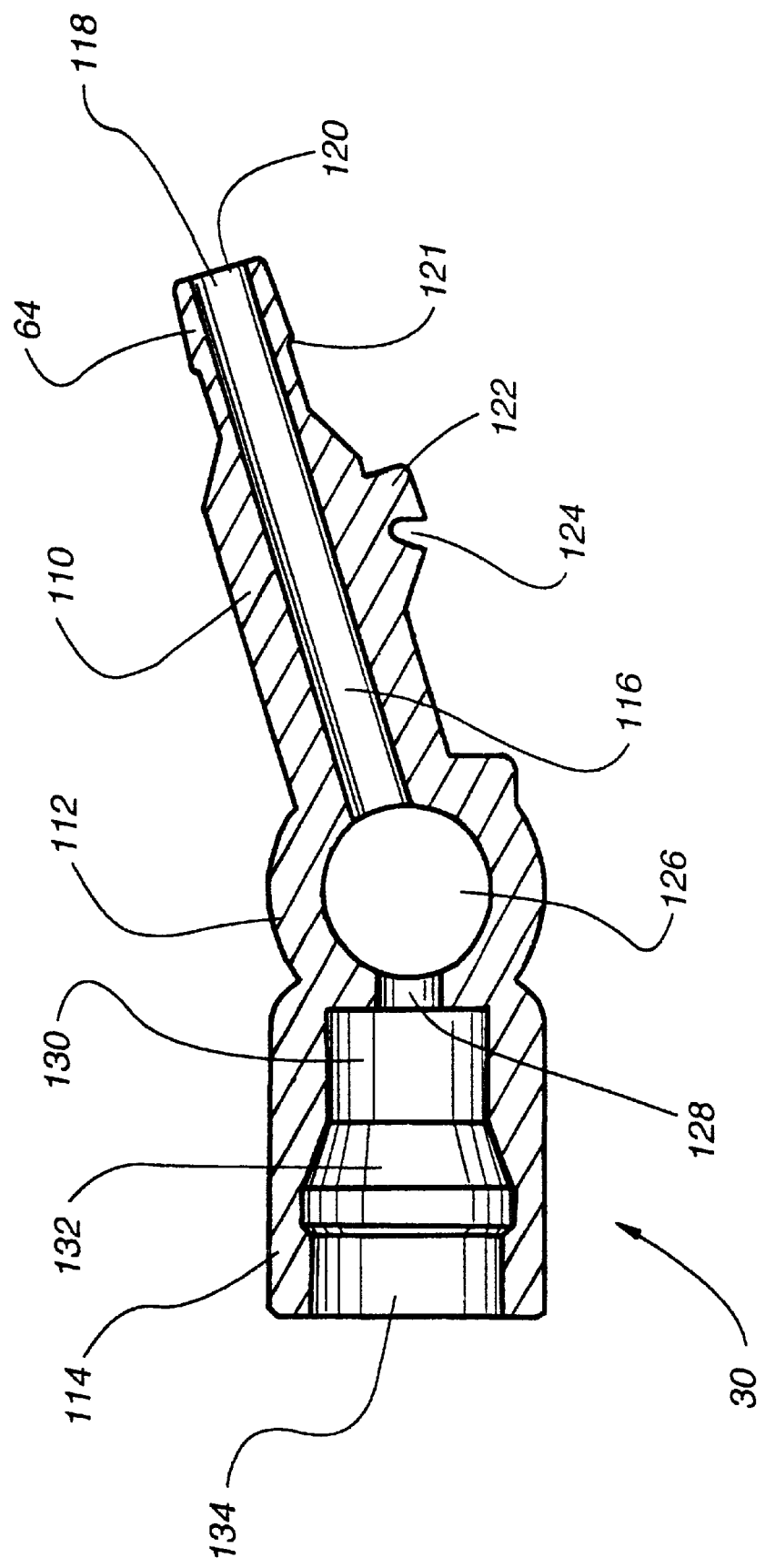
FIG. 5 illustrates a sectional view of the pressure control valve body of the hand piece assembly in accordance with one embodiment of the present invention.
Figure 10:
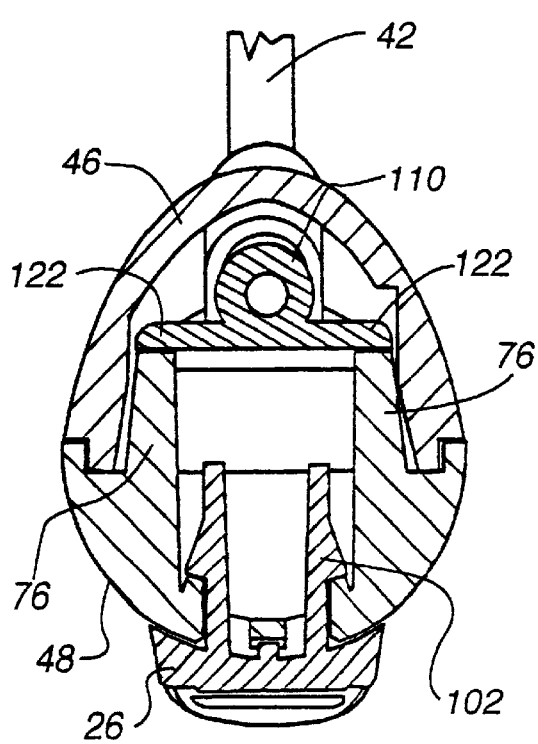
FIG. 10 is a sectional view of the hand piece assembly of one embodiment of the present invention, taken along section lines 10—10 of FIG. 3.

Referring to FIG. 5, the pressure control valve body 30 has an input section 110, an intermediate section 112, and an output section 114. The input section defines an inner fluid channel 116, having a first inner diameter 118, which at one end 120 is fluidly coupled to the hose 42 of the oral irrigator. In one example, the input section 110 is substantially cylindrical along its length and the inner diameter 118 is substantially constant along its length. An annular ridge 120 forming a nipple is positioned about the tip of the input section 110 to aide in securing the hose 42 thereabout. The input section 110 has laterally extending support members 122 having a groove 124 therethrough along the bottom portion of the support member 122. The groove 124 is adapted to rest on the top portion of the upwardly extending braces 76 of the lower handles member 48, and assists in maintaining the pressure control valve body 30 in a fixed position within the upper and lower handle members, as shown in FIG. 10.

The other end of the inner fluid channel 116 is fluidly coupled to the intermediate section 112 of the pressure control body 30. The intermediate section 112 defines a generally cylindrical chamber or bore 126 positioned orthogonally to the input section 110. As seen in FIG. 5, the intermediate section 112 has a substantially circular cross-section for receiving the cylindrical portion 64 of the pressure control valve gate 100.

The output section 114 is substantially cylindrical and positioned in-line with the inner fluid channel 116, and orthogonally to the intermediate section 112. The output section 114 defines an inner fluid channel 128 for directing fluid to the stop valve assembly 22. The output section 114 has a plurality of sections 130, 132, 134 having various interior diameters adapted to securably receive and couple with the stop valve body 136 and O-ring 138 (FIG. 2) to form a fluid tight seal.

Figure 6:
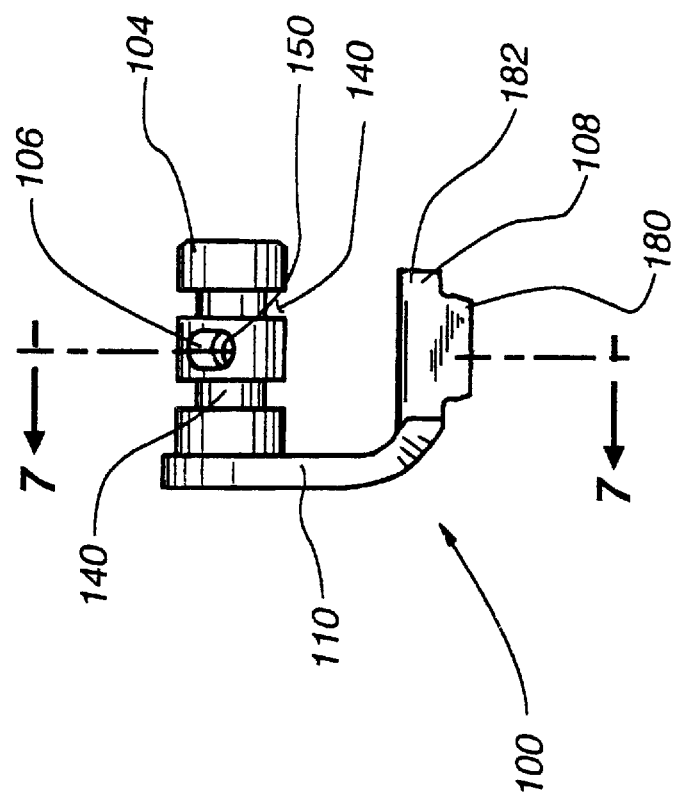
FIG. 6 illustrates a plan view of the valve gate of the hand piece assembly in accordance with one embodiment of the present invention.

Referring to FIG. 6, the valve gate 100 is shown having the orifice 106 bored orthogonally through the cylindrical portion 104 with the cylindrical portion 104 being coupled to the guide portion 108 by the control arm 110. In one example, the control arm 110 extends from one end of the cylindrical portion 104 to one end of the guide portion 108 to form a general U-shape, as shown in FIG. 6. The cylindrical portion 104 of the valve gate 100 defines annular slots 140 on each side of the orifice 106, each for receiving an O-ring 142 (FIG. 2). The O-rings 142 assist in forming a fluid tight seal within the intermediate chamber 112 of the valve body 30 upon insertion of the cylindrical portion 104 therein. The cylindrical portion 104 is adapted to fit snugly, but rotatably, within the intermediate section 112 of the pressure control valve body 30. When the cylindrical portion 104 is fully inserted within the intermediate section 112, the longitudinal axis of the orifice 106 bored therethrough aligns with the longitudinal axes of the inner fluid channels 116, 128 of the input and output sections 110, 114 to form a fluid flow path therebetween when the cylindrical portion 104 is properly oriented within and with respect to the intermediate section 112.

As the cylindrical portion 104 of the valve gate 100 rotates within the intermediate section 112 of the pressure control valve body 30, the orientation of the orifice 106 bored in the cylindrical portion 104 changes with respect to the inner fluid channels 116, 128 of the input and output sections 110, 114 of the pressure control valve body 30. Specifically, the periphery of the orifice 106 is rotatable from being aligned with the periphery of the inner fluid channels 116, 128 of the input and output sections 110, 114 (see FIG. 13), to being mis-aligned thereto (see FIG. 14).

Figure 11:
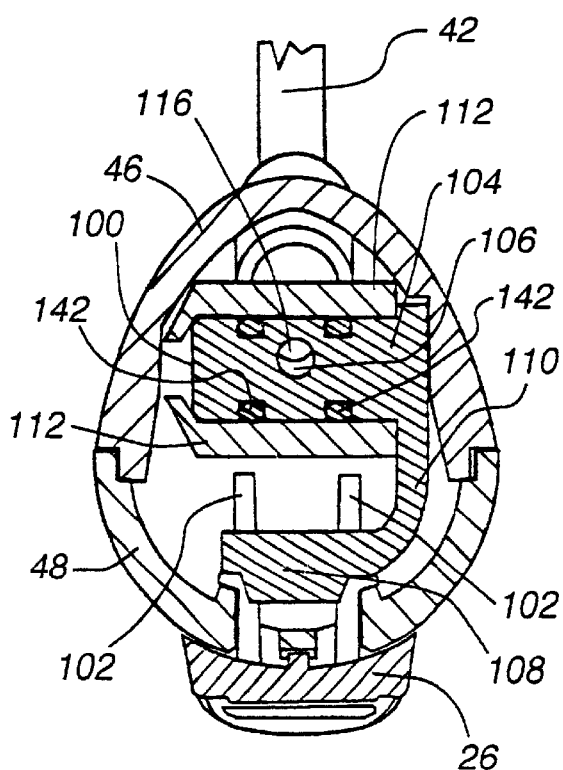
FIG. 11 is a sectional view of the hand piece assembly of one embodiment of the present invention, taken along section lines 11—11 of FIG. 10.
Figure 12:
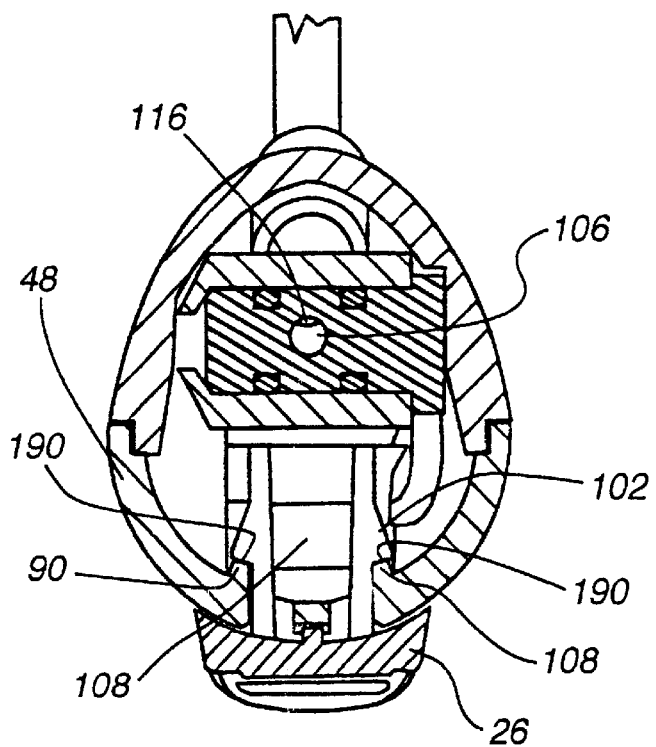
FIG. 12 is a sectional view of the hand piece assembly, as shown in FIG. 12 after the pressure control valve has been moved towards the partially closed position.

As the alignment of the orifice 106 changes with respect the inner fluid channels 116, 128, the effective interior diameter through which fluid can flow through the pressure control valve body 30 is altered and can be adjusted virtually infinitely to restrict or open, as desired, the flow path to control the flow pressure. This effect can bee seen by comparing FIG. 11 to FIG. 12, showing sectional views of the orifice 106, as the alignment of the orifice 106 with the inner fluid channel 116 of the input section of the pressure control valve body 30 changes from being partially aligned (FIG. 11) to less partially aligned (FIG. 12).

Figure 7:
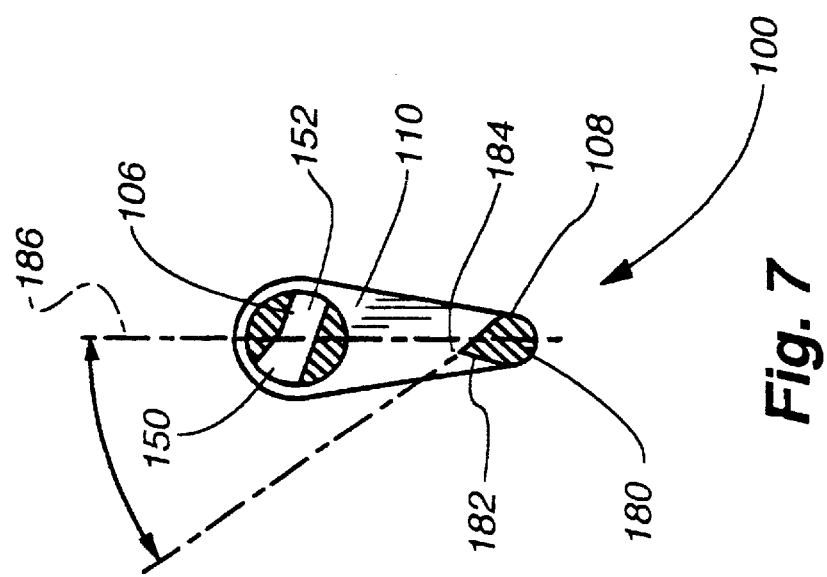
FIG. 7 illustrates a sectional view taken along section lines 7—7 of FIG. 6 illustrating the valve gate in accordance with one embodiment of the present invention.
Figure 13:
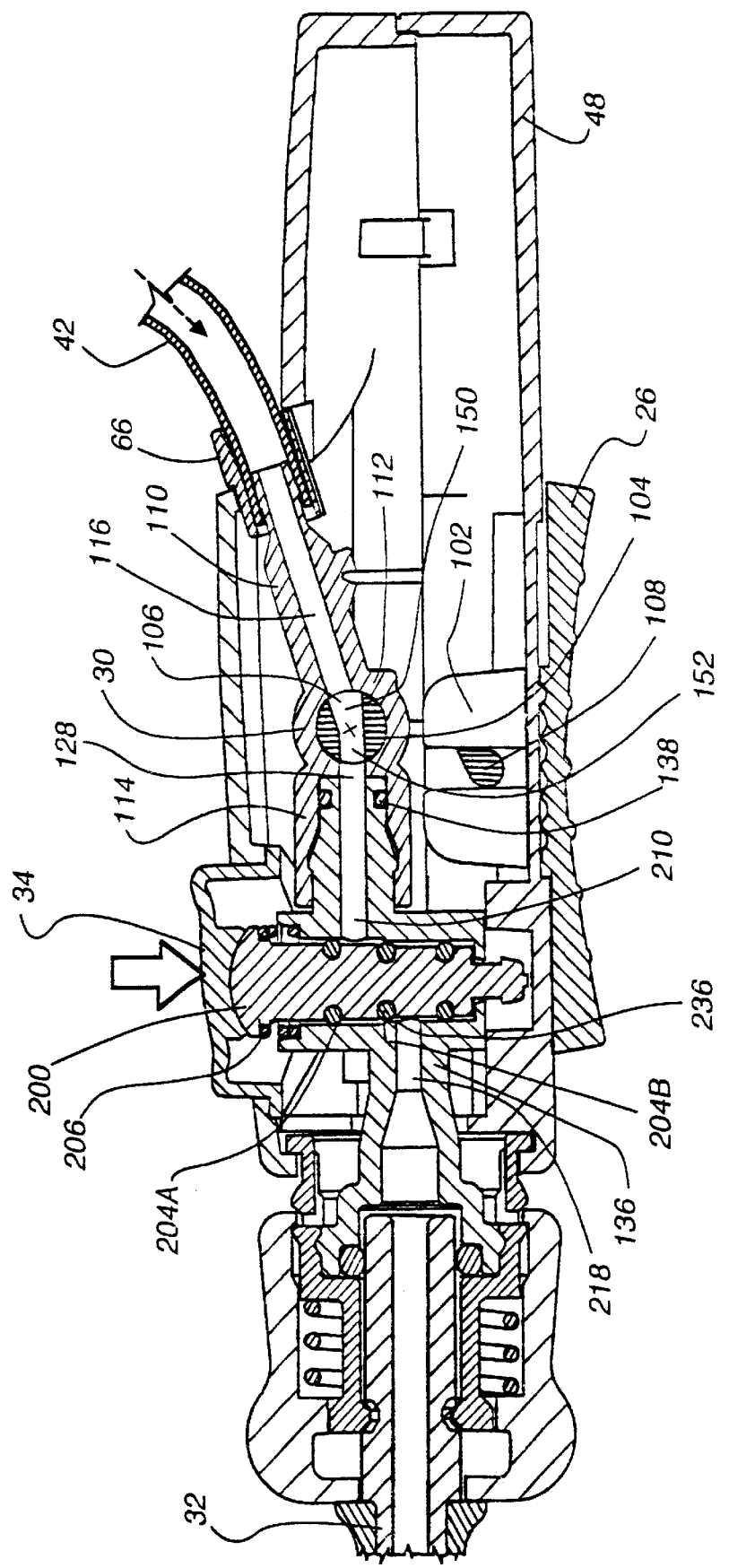
FIG. 13 is a sectional view of the hand piece assembly of one embodiment of the present invention with the stop valve in a depressed or closed position, and with the pressure control valve in the fully open position.

Referring to FIG. 7, the orifice 106 has an input channel 150 and an output channel 152, wherein the input channel 150 has an outwardly increasing interior diameter, and the output channel 152 has a substantially constant interior diameter. The input channel 150 is shaped to account for the angle which the inner fluid channel 116 of the input section 110 is offset from the inner fluid channel 128 of the output section 114. As shown in FIG. 13, the shape of the input channel 150 of the orifice 106 permits unrestricted fluid flow between the fluid channels 116, 128 when the orifice 106 is positioned in the fully open position. In one example, the input channel 150 has an inner diameter which increases from about 0.015 inches at the center of the cylindrical portion 104, to about 0.070 inches at the end of the cylindrical portion 104.

Figure 17:
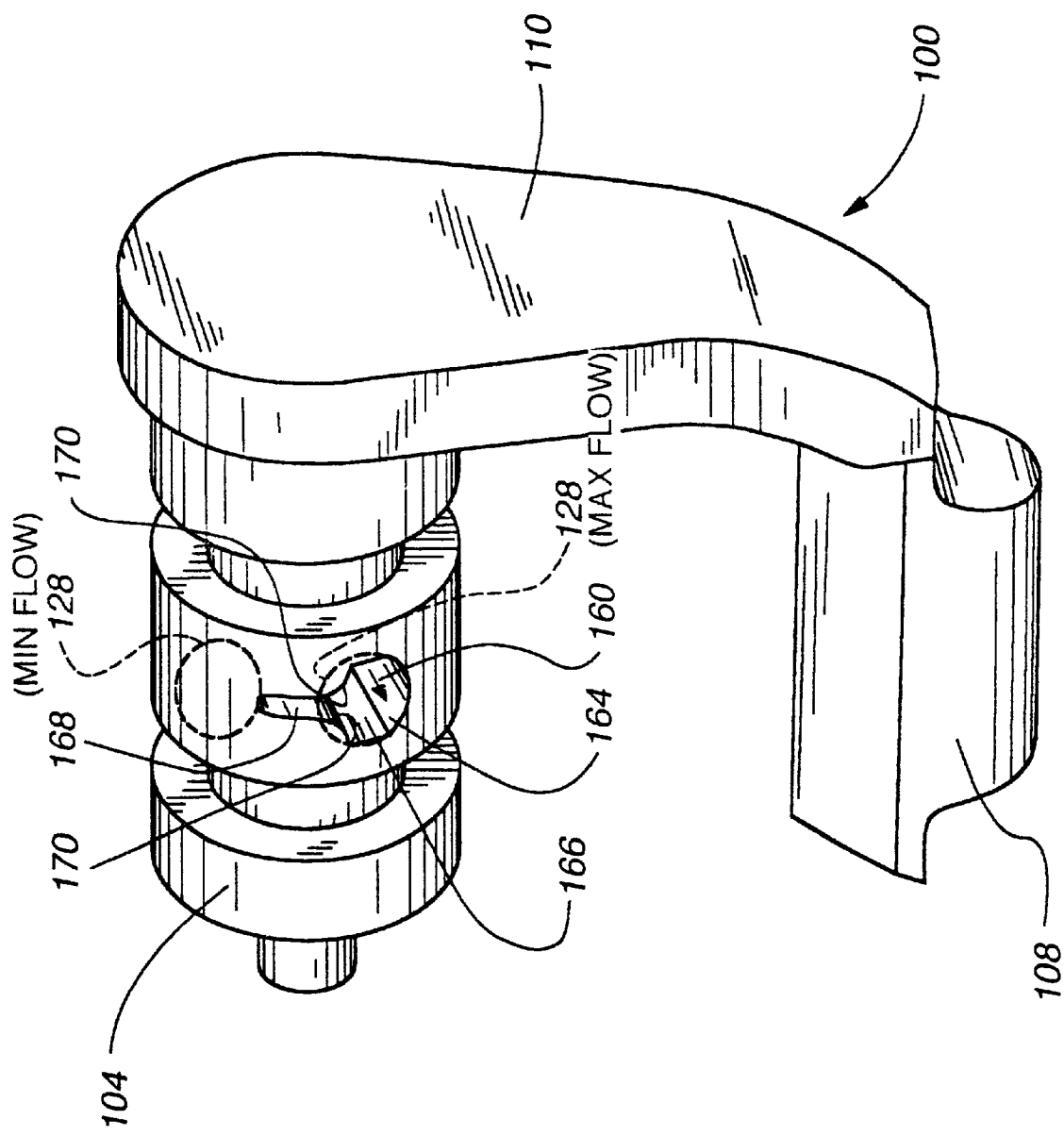
FIG. 17 illustrates a perspective view of an alternative embodiment of the valve gate of the hand piece assembly in accordance with the present invention.
Figure 18:
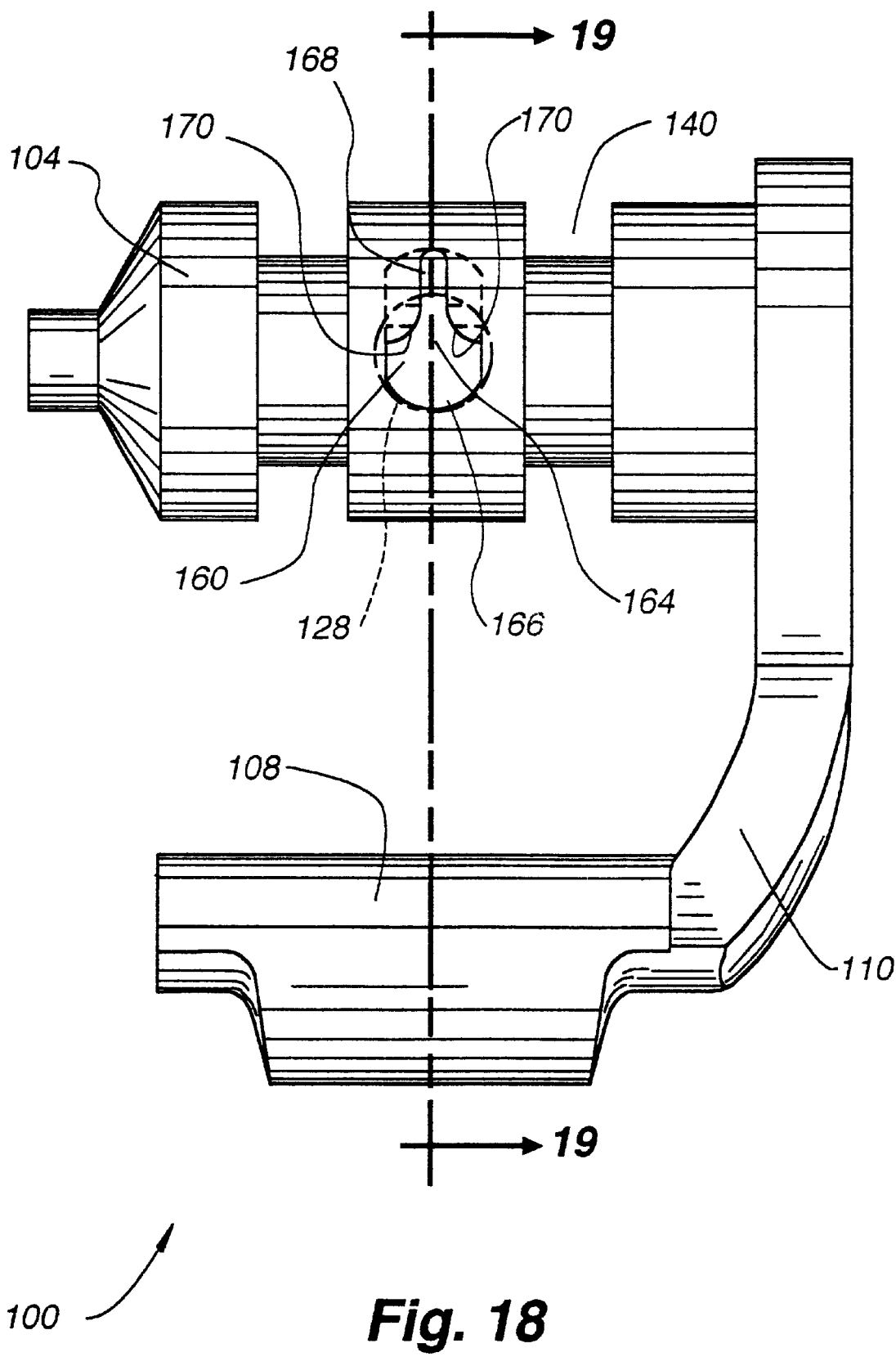
FIG. 18 illustrates a plan view of the alternative embodiment of the valve gate of FIG. 17 of the hand piece assembly in accordance with the present invention.
Figure 19:
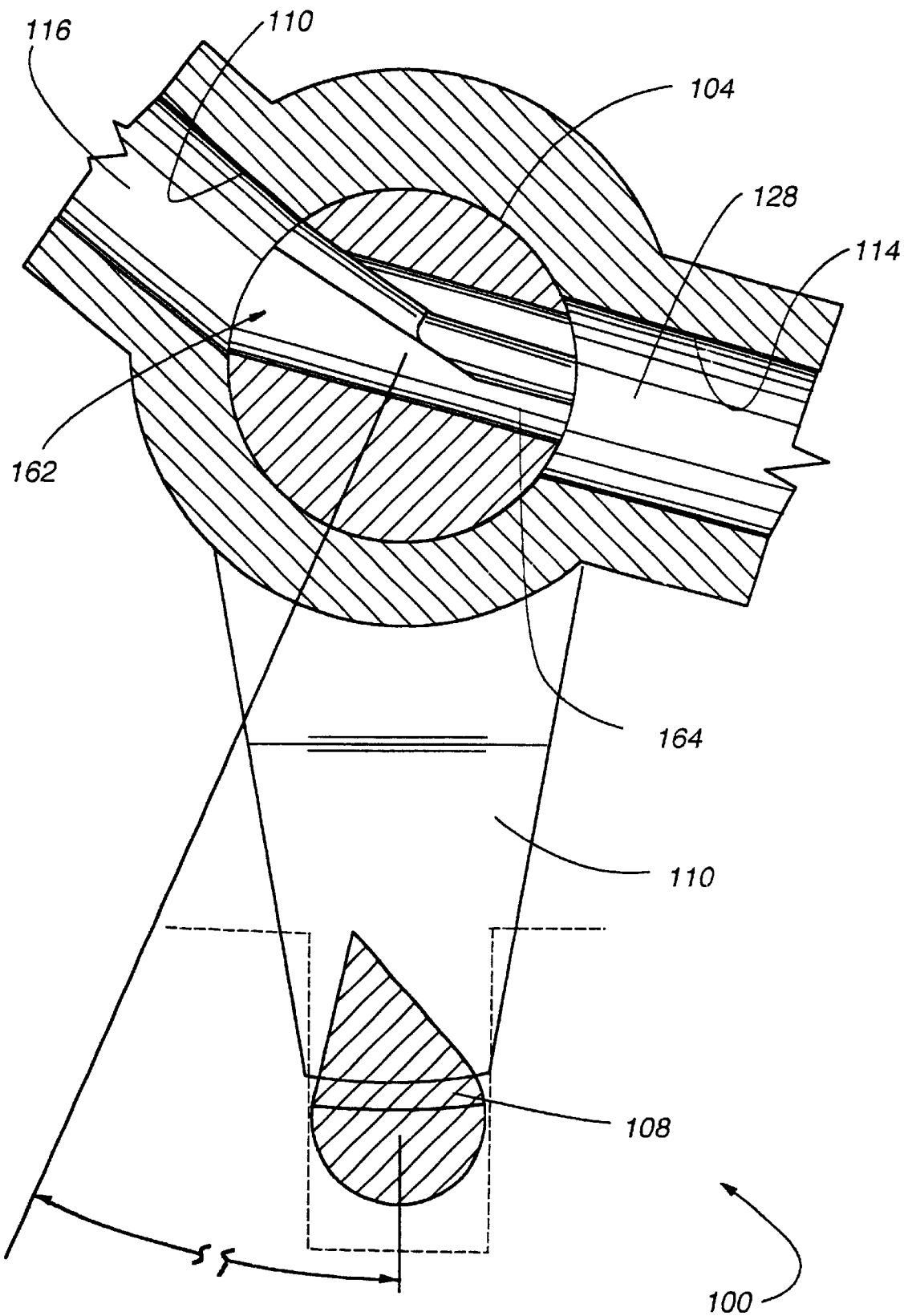
FIG. 19 illustrates a sectional view taken along section lines 19—19 of FIG. 18.

FIGS. 17–19 shows an alternative structure for an orifice 160, wherein the profile or shape of the orifice 160 transitions from an oval or cylindrical profile at the input channel 162 of the orifice, such as the profile of the input channel 150 shown in FIGS. 6 and 7, to an inverted "T" profile at the output channel 164 of the orifice 160 as shown in FIGS. 17–18. Along the output channel 164, the orifice 160 has a laterally extending bottom portion 166 and a narrow vertically extending top portion 168. Shoulders 170 extend along the length of the output channel 164 of the orifice 160 and form a transitional surface between the laterally extending bottom portion 166 and the narrow vertically extending top portion 168.

The inverted "T" shaped orifice 160 permits a more drastic reduction in the effective diameter of the fluid flow path through the pressure control valve body 30 as the cylindrical portion 104 of the valve gate 100 is rotated from a maximum flow orientation to a minimum flow orientation within the intermediate portion 112 of the valve body 30. In particular, when the cylindrical portion 104 of the valve gate 100 is positioned in the maximum flow orientation, the laterally extending bottom portion 166 of the output channel 164 of the orifice 160 is substantially aligned with the inner fluid channel 128 of the output section 114, as shown in FIGS. 17–18. When the cylindrical portion 104 of the valve gate 100 is positioned in the minimum flow orientation, the narrow vertically extending top portion 168 of the output channel of the orifice 160 is substantially mis-aligned with the inner fluid channel 128 of the output section 114, as shown in FIG. 17. The fluid flow in the minimum flow orientation is only that fluid that bypasses the cylindrical portion 104 between the O-rings 142. As the cylindrical portion 104 of the valve gate 100 is moved from the maximum flow orientation to the minimum flow orientation, the effective diameter of fluid flow path through the orifice 160 is drastically reduced. Therefore, the inverted "T" shaped orifice provides a quicker reduction in pressure of the fluid delivered through the hand piece.

Figure 14:
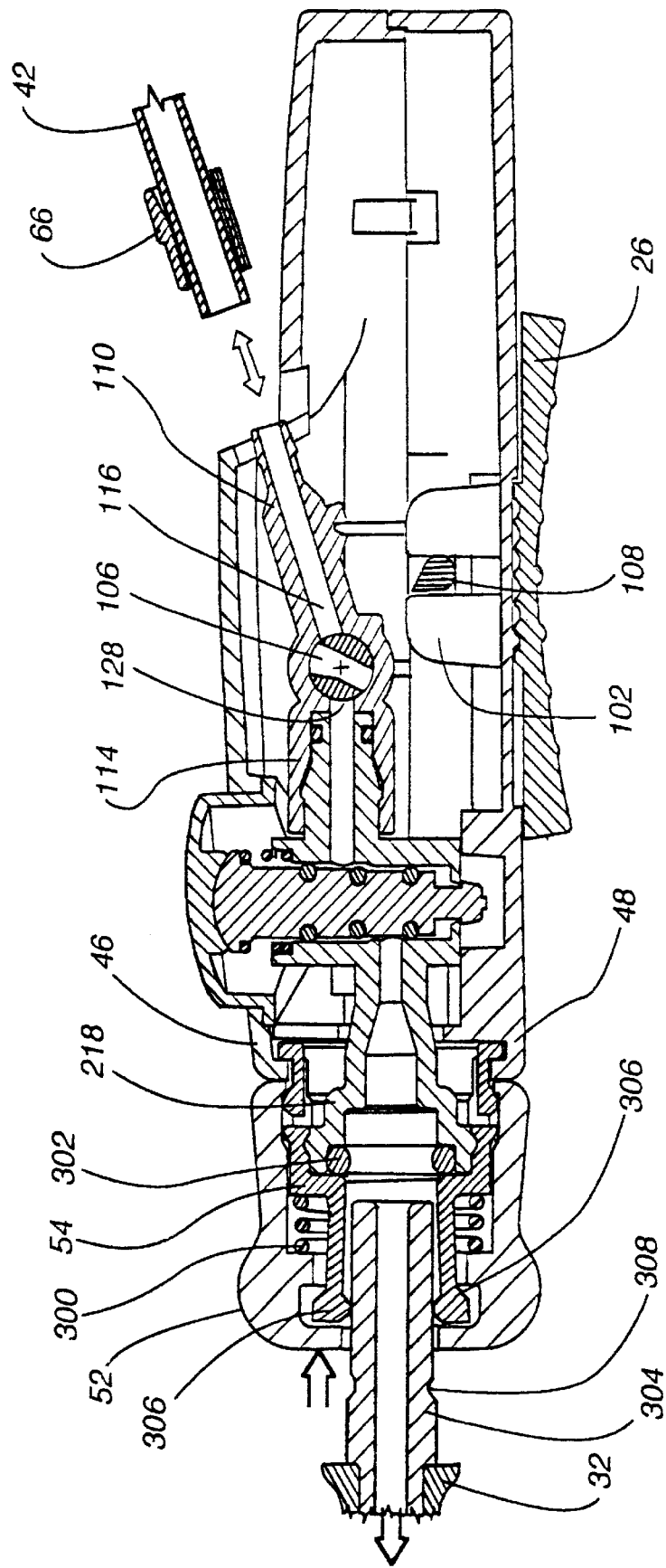
FIG. 14 is a sectional view of the hand piece assembly of one embodiment of the present invention showing the attachment or removal of components to the hand piece assembly, while the pressure control valve is in the fully closed position.

As seen in FIG. 7, the guide portion 108 of the valve gate 100 has lower semicircular portion 180 and a triangular or v-shaped upper portion 182 terminating at an apex 184. The semicircular portion 180 reduces the contact friction between the guide portion 108 and the yokes 102 of the slide control 26 as the valve gate 100 is moved. The V-shaped portion 182 assists in limiting the extent to which the cylindrical portion 104 of the valve gate rotates within the pressure control valve body 30 in response to linear movement of the slide control 26. In one example, the apex 184 of the V-shaped portion 182 is offset 15 degrees (see FIG. 7) from a vertical centerline 186 so each side of the V-shaped upper portion 182 of the guide portion 108 aligns in parallel or flush with respect to the sides of the yokes 102 when the slide control 26 is positioned at either end of its actuating length, as shown in FIGS. 13 and 14.

Figure 15:
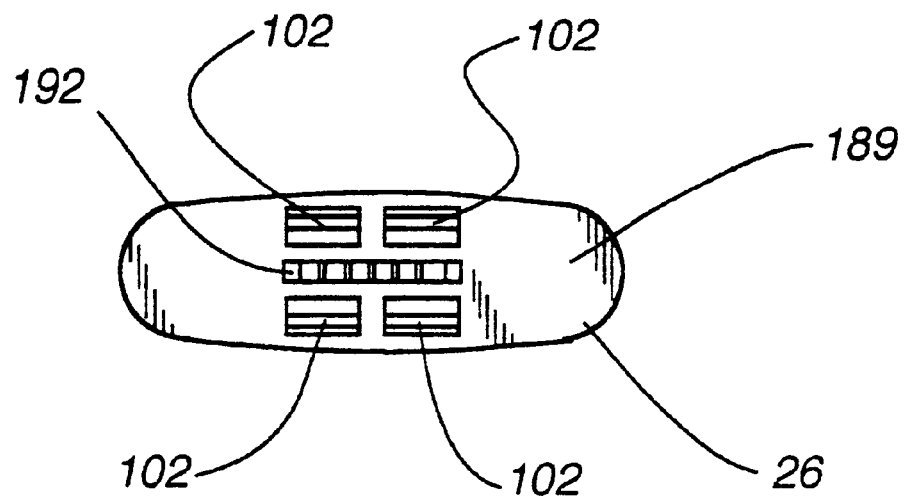
FIG. 15 illustrates a bottom view of the slide control of the hand piece assembly in accordance with one embodiment of the present invention.

Referring to FIGS. 2, 3, and 15, the slide control 26 has a plurality of upwardly extending yokes 102 which are arranged in pairs and aligned in series along the length of the interior surface 189 of the slide control 26. Each pair of the series-positioned yokes 102 are adapted to be inserted through the rectangular slots 84 formed in the lower handle member 48. As shown in FIGS. 2 and 12, the yokes 102 each have an outwardly extending slide bearing surface 190 adapted to engage and slide upon the respective raised guides 90 of the lower handle member 48. The slide bearing surfaces 190 establish a constant and smooth movement between the slide control 26 and the lower handle member 48. With respect to each series pair of yokes 102, a gap 110 (FIGS. 2 and 3) is formed between each yoke so that the guide portion 108 of the pressure control valve gate 100 can be positioned therebetween.

Additionally, as shown in FIGS. 3 and 15, the interior surface 189 has a plurality of raised indices 192 positioned between the pairs of yokes 102. These raised indices 192 frictionally engage the protrusion 88 on the exterior surface of the bridge portion 86 of the lower handle member 48 to provide the user with tactile and audible feedback as the slide member 26 is moved along the lower handle member. In one example, the raised indices 192 are substantially equally spaced so that as the slide control 26 moves linearly along its actuating length along the lower handle member 46, the protrusion 88 sequentially engages the raised indices 192, thereby providing the user with graduated detent positions for the slide control 26 along the lower handle member. An audible "click" sound may also be present depending on the relative dimensions of the protrusion 88 and the raised indices 192.

The slide control 26 includes the interior surface 189 and a curved exterior surface 194, as shown in FIGS. 2 and 3. The curved exterior surface 194 can be provided with a surface treatment 196 to provide the user with a desired tactile feel. In one example, the exterior surface 194 of the slide control 26 is sized and curved to conform to the shape of a user's thumb so that the user can easily manipulate the linear position of the slide control 26 relative to the lower handle member 48.

The interaction between the slide control 26, the yokes 102, and the valve gate 100 is to convert the linear motion of the slide control 26 to rotary motion of the cylindrical portion 104, including the orifice 106 of the valve gate 100, within the valve body 30. The slide control 26 being linearly movable has been found, in accordance with the present invention, to be more desirable from a user's point of view for controlling pressure than a rotary knob, due to the ease with which the pressure adjustment can be made by the user.

Figure 8:
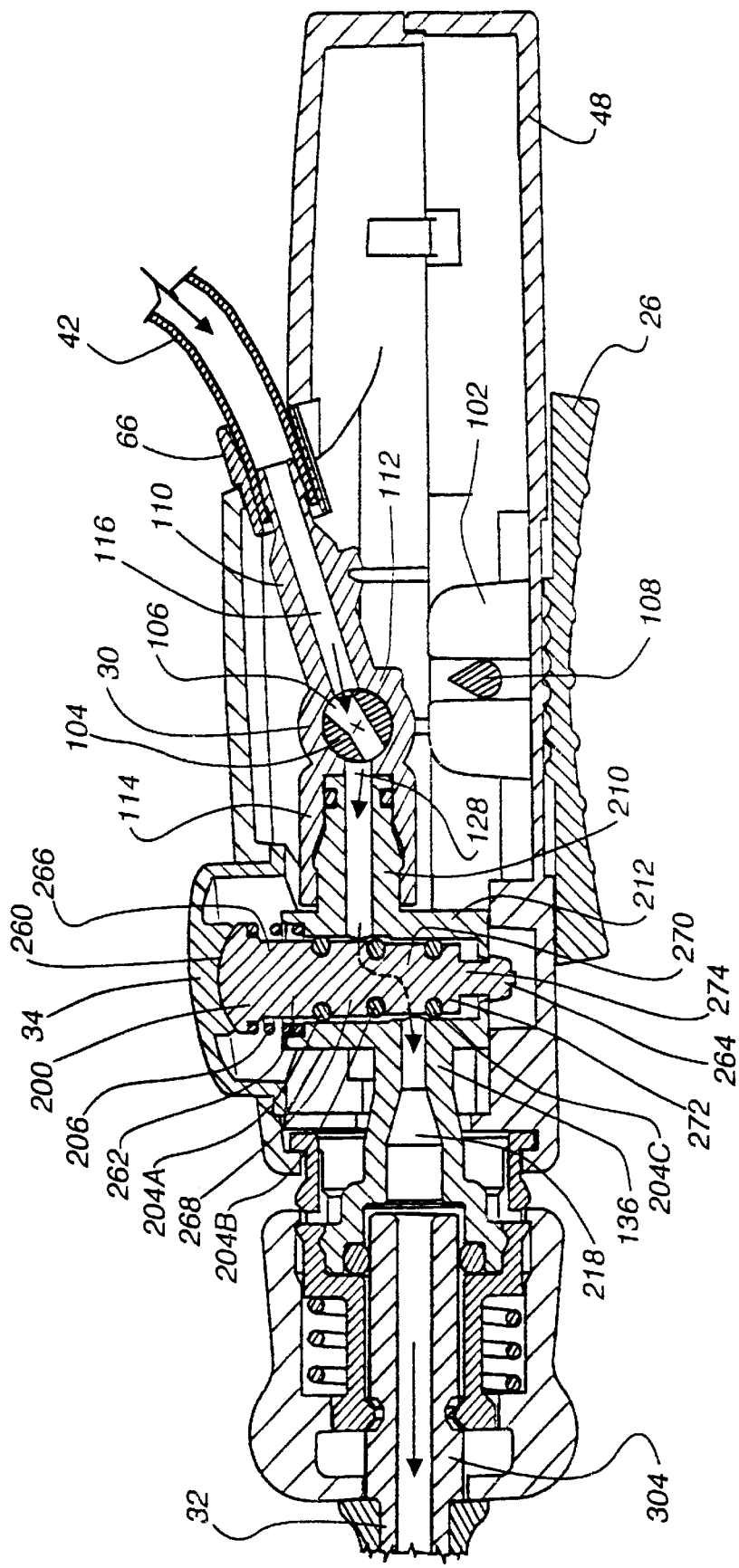
FIG. 8 illustrates a sectional view of the hand piece assembly of one embodiment of the present invention with the pressure control valve in a partially open position.
Figure 9:
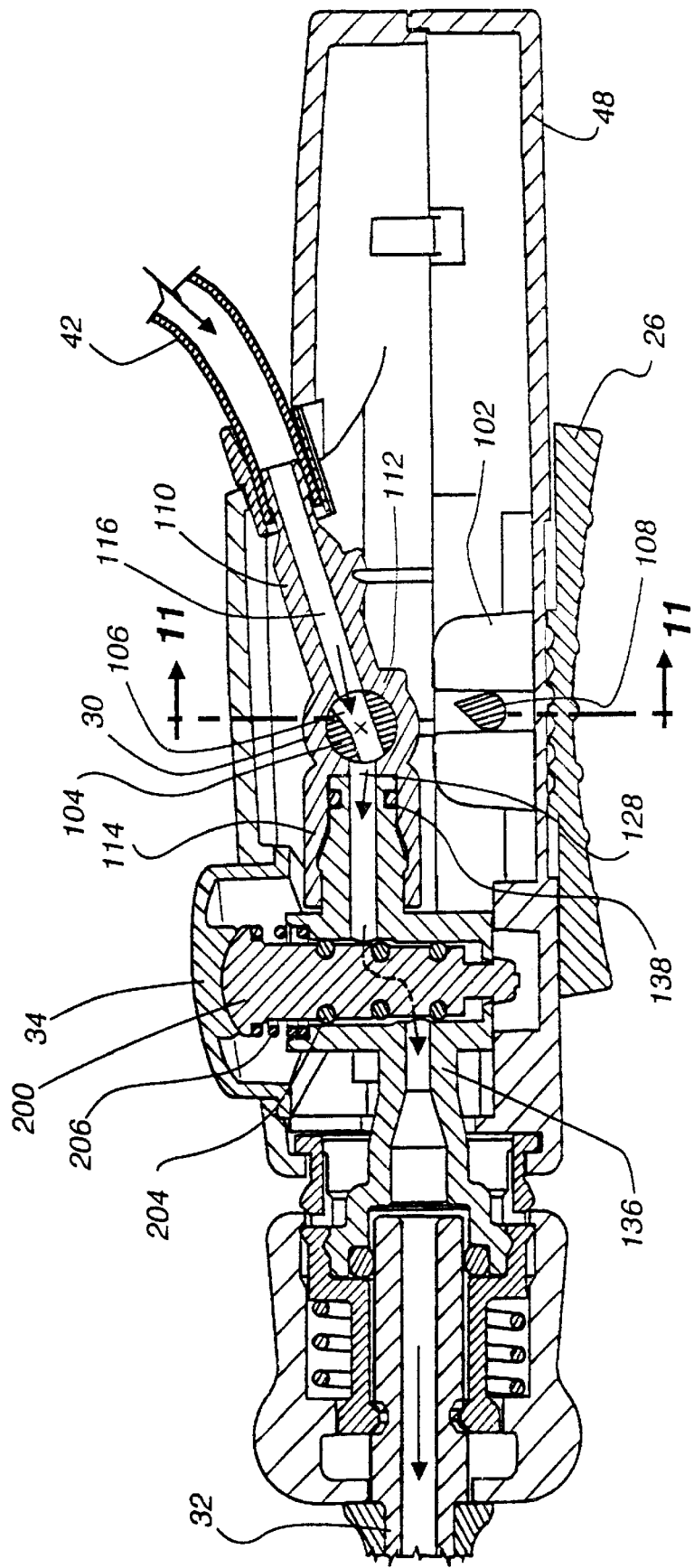
FIG. 9 illustrates a sectional view of the hand piece assembly of one embodiment of the present invention as the pressure control valve is moved towards a fully open position.

Having described the structure of the pressure control valve assembly 24, the sequence in which the valve moves from a closed position to an open position can be seen with references to FIGS. 3, 8, 9, and 13. In FIG. 3, the slide control 26 is in the rightmost position which orients the orifice 106 of the valve gate 100 in a substantially closed position within the pressure control valve body 30. As seen in FIG. 3, the fluid flow path from the input section 110 through the intermediate section 112 to the output section 114 of the valve body 30 is substantially constricted due to the orientation of the orifice 106. Referring to FIG. 8, as the slide control 26 is moved towards the left, the yokes 102 exert a force upon the guide portion 108 of the valve gate, which rotates the cylindrical portion 104 of the valve gate clockwise and orients the orifice 106 into a more aligned and open position with respect to the inner fluid channels 116, 128 of the input and output sections 110, 114 of the valve body 30. Referring to FIG. 9, as the slide control 26 moves farther to the left, the orifice 106 continues to rotate in a clockwise direction within the valve body 30. Finally, in FIG. 13, as the slide control 26 is moved to its leftmost position, the orifice 106 is oriented so that a fully opened fluid flow path is formed within the pressure control valve body 30. Accordingly, it can be seen that as the slide control 26 moves along the lower handle member 48, the cylindrical portion 104 of the valve gate 100 rotates within the pressure control valve body 30 to form fluid flow paths of varying effective diameters therein, which thereby regulates the pressure of the fluid flow passing through the hand piece assembly.

From FIGS. 3, 8, 9, and 13, it can be seen that the guide portion 108 of the valve gate 100 moves along an arc with respect to the intermediate section 112 of the valve body as the slide control 26 travels linearly along the exterior of the lower handle member. In this manner, the guide portion 108 and control arm 110 of the valve gate 100 convert the linear motion of the slide control 26 into a proportional amount of rotational movement of the cylindrical portion 104 and orifice 106 within the valve body 30. In one example, 0.400 inches of linear travel of the slide control 26 along its actuating length rotates the cylindrical portion 104 of the valve gate 100 by about 60 degrees, and varies the flow rate from about 90 psi to about 10 psi.

After the fluid flows through the pressure control valve assembly 24 of the hand piece assembly 20, the fluid then flows into the stop valve assembly 22. The stop valve assembly 22 permits the user of the hand piece to momentarily stop or pause the fluid flow through the hand piece. The stop valve assembly 22 includes a push button 34, a plunger 200 having varying diameters and circumferential notches 202 along its body, a set of O-rings 204 positionable within the circumferential notches 202 of the plunger 200, a spring 206 for outwardly biasing the plunger 200 and the push button 34, and a stop valve body 136 as shown in FIGS. 2, 8, 9 and 13. The spring 206 provides an outward bias force on the plunger 200 so that the fluid flow path through the stop valve body 136 is maintained normally open or un-restricted. In one example, the spring 206 is a compression type spring having open ends, such as Model No. TW-020MWCS available from Colorado Coiling of Longmont, Colo.

Figure 4:
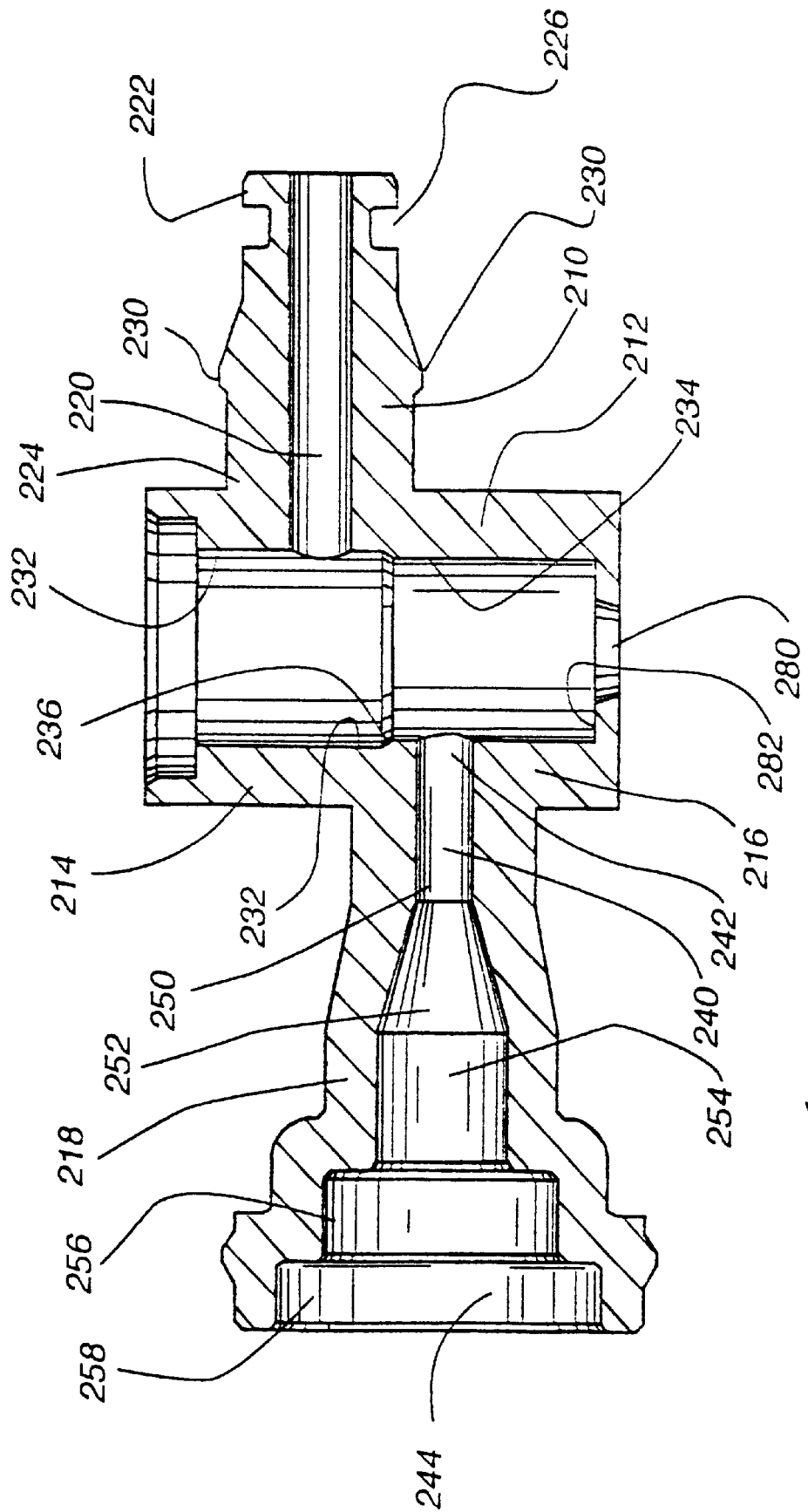
FIG. 4 illustrates a sectional view of the stop valve body of the hand piece assembly in accordance with one embodiment of the present invention.

Referring to FIG. 4, the stop valve body 136 has an input chamber 210, an intermediate chamber 212 having an upper 214 and lower 216 portion, and an output chamber 218. These three fluid chambers define a portion of the fluid flow path through the hand piece assembly.

The input chamber 210 defines an inner fluid channel 220 of uniform inner diameter and is adapted to be coupled, at one end 222, to the output section 114 of the pressure control valve body 30. The input chamber 210 is also fluidly coupled, at its opposing end 224, to the upper portion 214 of the intermediate chamber 212. The input chamber 210 has an annular channel 226 on its exterior surface adapted to receive an O-ring 138 (FIG. 2) for sealing and engaging the output section 114 of the pressure control valve body 30. In one example, the O-ring 138 is made of Buna-N material having a shore hardness of 70 and a tensile strength of 2,000 psi minimum, and such an O-ring is available from Real Seal of Escondido, Calif. This type of O-ring is able to be used in the other applications described herein.

In one embodiment of the invention shown in FIG. 4, the input chamber 210 of the stop valve body 136 and the output chamber 114 of the pressure control valve body 30 are matingly keyed so that the proper orientation of the pressure control valve body 30 is maintained after being coupled to the stop valve body 136. An annular ridge 230 forming a nipple is positioned about the tip 222 of the input chamber 210 to aide in securing the stop valve body 136 to the pressure control body 30.

The intermediate chamber 212 has an upper portion 214 defining a first interior diameter 232, and a lower portion 216 defining a second interior diameter 234. In one example of the present invention, the first interior diameter 232 is greater than the second interior diameter 234 so that an angled frustoconical bearing surface 236 is formed between the upper and lower portions 214, 216 of the intermediate chamber 212.

The output chamber 218 of the stop valve body 136 defines an inner fluid channel 240 and is fluidly coupled, at one end 242, to the lower portion 216 of the intermediate chamber 212, and is adapted to be coupled at its opposing end 244 to the input end of the jet tip 32. The output chamber 218 has five interior sections, wherein a first section 250 has a constant interior diameter, a second section 252 has a frustoconical increasing interior diameter, a third section 254 has a constant interior diameter greater than the interior diameter of the first section 250, a fourth section 256 has a greater interior diameter than the third section 254, and a fifth section 258 has a greater interior diameter than the fourth section 256.

The plunger 200 of the stop valve assembly 22 is adapted to be controllably positioned within the intermediate chamber 212 of the stop valve body 136. Referring now to FIG. 8, the plunger 200 has a curved top portion 260 and an elongated body 262 having various sections terminating at a tip portion 264. The elongated body has, in one example, five sections 266, 268, 270, 272, 274 of decreasing diameters adapted to fit within and correspond to the interior diameters of the intermediate chamber 212 of the stop valve body 136. Between the first four sections 266, 268, 270, 272 of the elongated body, annular slots or circumferential notches 202 are provided about the elongated body for each receiving an O-ring 204 therein to form a fluid tight seal when the plunger 200 is inserted into the stop valve body 136. The tip portion 264 of the plunger 200 has a frustoconical periphery adapted to be inserted through the bottom opening 280 (FIG. 4) of the intermediate chamber 212 when the plunger 200 is initially positioned within the intermediate chamber 212 during manufacturing. The diameter of the fifth section 274 of the plunger is sized so that a bearing surface is formed on the interior of the tip portion 264 which engages a bottom portion 282 (FIG. 4) of the intermediate chamber 212, which prevents the plunger 200, spring 206, and push button 34 assembly from excessive upward movement.

As can be seen in FIGS. 2 and 3, the push button 34 has a collar 284 which engages an interior shoulder 286 of the upper handle member 46 to retain the push button 34 within the interior of the upper handle member 46. The push button 34 also defines within its interior a curved surface 288 adapted to receive the curved top portion 260 of the plunger.

FIGS. 3 and 8 illustrate the plunger 200 in its normal or detent position where the input chamber 210 and output chamber 218 of the stop valve body 136 are in fluid communications through the intermediate chamber 212. The plunger 200 and intermediate chamber 212 are designed so that when the plunger is in the uncompressed or default position, fluid flows from the input chamber 210 into the intermediate chamber 268, 270 between the first and third O-rings 204, around the second and third sections 268, 270 of the body of the plunger 200, and out through the output chamber 218. In this normal default position of the plunger, a fluid channel is formed within the intermediate chamber 212 which fluidly couples the input chamber 210 to the output chamber 218. The fluid channel is formed between the first O-ring and third O-ring along the second and third sections 268, 270 of the body of the plunger and within the intermediate chamber 212. Specifically, the first O-ring 204A (FIG. 8) is adapted to provide a fluid-tight seal so that fluid from the input chamber 210 does not flow above the first O-ring 204A into the first section 266 of the plunger. The third O-ring 204C is adapted to provide a fluid-tight seal with the second interior diameter 234 of the intermediate chamber 212, so that pressurized fluid received from the input chamber 210 does not travel below the third O-ring 204C and reach the fourth section 272 of the plunger or beyond.

FIG. 13 illustrates the plunger 200 in its depressed position wherein the fluid flow between the input chamber 210 and output chamber 218 is blocked, and fluid flow therebetween is interrupted until the push button 34 and plunger 200 are released. When the plunger 200 is in the depressed or closed position, the second O-ring 204B engages the frustoconical bearing surface 236 between the upper and lower portions 214, 216 of the intermediate chamber 212. A fluid-tight seal is thus formed between the first and second O-ring 204A, 204B above the lower portion 216 of the intermediate chamber 212, so that no fluid flows into the output chamber 218 nor into the jet tip 32.

In this way, when the plunger 200 is in the depressed position, the fluid conductivity between the input chamber 210 and output chamber 218 is disrupted until the plunger is released upwardly into its normal default position. Once the push button 34 is released, the fluid pressure delivered through the hand piece assembly increases to the pressure previously established by position of the slide control 26.

As described above, the output chamber 218 of the stop valve body 136 is in fluid communications with the jet tip 32. The knob 52 and collet 54 assembly permit the user to attach or remove various jet tips to the hand piece assembly. The knob and collet assembly include the knob 52, the collet 54 positioned within the knob 52, a spring 300 positioned between the knob and collet, and an O-ring 302.

Referring to FIGS. 2 and 3, the knob 52 is generally circular and adapted to house therein the collet 54, the spring 300, the input portion 304 of the jet tip, the O-ring 302, and the output portion 218 of the stop valve body 136. Referring to FIGS. 3 and 14, as the knob 52 is moved axially in translation by the user towards the upper and lower handle members 46, 48, the spring 300 is compressed and the tines 306 of the collet 54 move radially outward to a release position so that the input portion 304 of the jet tip 32 can be inserted or removed from within the knob 52 and collet 54 assembly. When the knob 52 is released and moves by the force of the spring 300 axially away from the upper and lower handle members 46, 48, the tines 306 of the collet move radially inwards to a closed position and clasp about a notch 308 (FIG. 14) the input portion 304 of the jet tip 32 to secure it within the collet 54. A suitable knob, spring, collet, and O-ring are described in U.S. Pat. No. 5,399,089, incorporated by reference above.

In operation, after a jet tip 32 is attached to the hand piece assembly 20 of the present invention, which is attached to the fluid supply tube 42 of the oral irrigator, the user can adjust the pressure of the fluid delivered out of the jet tip 32 by varying the linear position of the slide control 26. The slide control 26 rotates the orifice 106 bored within the cylindrical portion 104 of the valve gate 100 to reduce the effective internal diameter of the fluid flow path within the hand piece assembly, as described above. The user can then depress the push button 34 to temporarily stop or pause the fluid flow out from the jet tip 32. When the push button 34 is released, the fluid pressure delivered through the hand piece assembly increases to the pressure previously established by the slide control.

It should be noted that while the pressure control valve and stop valve assemblies 24, 22 have been shown and described as preferably contained within the hand piece assembly for ease of use, both the pressure control valve and stop valve assemblies can be variously located on the oral irrigator base or the hand piece, depending on the particular application.

A presently preferred embodiment of the present invention and many of its improvements have been described with a degree of particularity. It should be understood that this description has been made by way of example, and that the invention is defined by the scope of the following claims.

What is claimed is:

1. A pressure control valve for a handle of an oral irrigation device, comprising:

a valve body having an input section defining an input fluid flow path, an intermediate section having a substantially cylindrical bore therethrough, and a output section defining an output fluid flow path, said input fluid flow path fluidly coupled to said output fluid flow path through said bore;

a valve gate having a cylindrical portion, a guide portion, and a control arm having a first end coupled to said cylindrical portion and having a second end coupled to said guide portion, said cylindrical portion having an orifice bored therethrough; and a slide control coupled to guide portion of the valve gate, so that as the slide control moves linearly, the cylindrical portion of the valve gate correspondingly rotates within the bore of the valve body.

2. The pressure control valve of claim 1, wherein the cylindrical portion of the valve gate has a pair of recessed annular channels about the orifice for receiving a pair of O-rings.

3. The pressure control valve of claim 1, wherein the guide portion has a V-shaped portion.

4. The pressure control valve of claim 1, wherein the guide portion has a semicircular portion.

5. The pressure control valve of claim 1, wherein the cylindrical portion is rotatable between a first orientation where the orifice is substantially aligned between the input fluid flow path and the output fluid flow path, to a second orientation where the orifice is substantially mis-aligned between the input fluid flow path and the output fluid flow path.

6. The pressure control valve of claim 1, wherein the slide control has pair of upwardly extending yokes with a gap formed therebetween, and said guide portion is positioned in the gap portion.

7. A handle assembly for an oral irrigator, comprising:

a housing;

a pressure control valve, comprising:

a valve body having an input section defining an input fluid flow path, an intermediate section having a substantially cylindrical bore therethrough, and a output section defining an output fluid flow path, said input fluid flow path fluidly coupled to said output fluid flow path through said bore;

a valve gate having a cylindrical portion, a guide portion, and a control arm having a first end coupled to said cylindrical portion and having a second end a coupled to said guide portion, said cylindrical portion having an orifice bored therethrough; and a slide control positioned on the housing, the slide control being coupled to guide portion of the valve gate, so that as the slide control moves linearly along a portion of the housing, the cylindrical portion of the valve gate correspondingly rotates within the bore of the valve body.

8. The pressure control valve of claim 7, wherein the housing has a protrusion and the interior surface of the slide control has a plurality of raised indices adapted to contact the protrusion as the slide control is linearly moved along the housing.

9. The pressure control valve of claim 7, wherein the input section has a laterally extending support member thereon for supporting the valve body within the housing of the oral irrigation device.

10. The handle assembly of claim 7, further comprising:

a stop valve assembly for momentarily stopping the flow of fluid through the handle assembly.

11. The handle assembly of claim 10, wherein the stop valve assembly further comprises:

a plunger having a generally elongated body and plurality of recessed annular rings along the body, a plurality of O-rings adapted to each be placed within one of the annular rings; and a stop valve body having an input chamber defining an input fluid flow path, an intermediate chamber having a first interior diameter and a second interior diameter, and an output chamber defining an output fluid flow path, said input fluid flow path fluidly coupled to said output fluid flow path through said intermediate chamber, so that as said plunger is depressed within said stop valve body, the plunger blocks the fluid flow with said intermediate chamber.

12. The handle assembly of claim 11, wherein the first interior diameter is smaller than said second interior diameter within said intermediate chamber of the stop valve assembly.

13. The handle assembly of claim 10, wherein the stop valve assembly further comprises a spring biasing said plunger in a normally open within said stop valve body.

14. An oral irrigation system for delivering pressurized fluid along a tube to a jet tip, comprising:

handle assembly having a housing adapted to receive the jet tip, said handle assembly having a fluid input adapted to be coupled to said tube and a fluid outlet port adapted to be coupled to the jet tip, the handle assembly comprising:

a pressure control valve, comprising:

a valve body having an input section defining an input fluid flow path, an intermediate section having a substantially cylindrical bore therethrough, and a output section defining an output fluid flow path, said input fluid flow path fluidly coupled to said output fluid flow path through said bore;

a valve gate having a cylindrical portion, a guide portion, and a control arm having a first end coupled to said cylindrical portion and having a second end coupled to said guide portion, said cylindrical portion having an orifice bored therethrough; and a slide control positioned on the housing, the slide control being coupled to guide portion of the valve gate, so that as the slide control moves linearly along a portion of the housing, the cylindrical portion of the valve gate correspondingly rotates within the bore of the valve body.

15. The oral irrigation system of claim 14, further comprising:

a stop valve assembly for momentarily stopping the flow of fluid through the handle assembly.

16. The oral irrigation system of claim 15, wherein the stop valve assembly further comprises:

a plunger having a generally elongated body and plurality of recessed annular rings along the body;

a plurality of O-rings adapted to each be placed within one of the annular rings; and a stop valve body having an input chamber defining an input fluid flow path, an intermediate chamber having a first interior diameter and a second interior diameter, and an output chamber defining an output fluid flow path, said input fluid flow path fluidly coupled to said output fluid flow path through said intermediate chamber, so that as said plunger is depressed within said stop valve body, the plunger blocks the fluid flow with said intermediate chamber.

17. The oral irrigation system of claim 16, wherein the first interior diameter is smaller than said second interior diameter within said intermediate chamber of the stop valve assembly.

18. The oral irrigation system of claim 16, wherein the stop valve assembly further comprises a spring biasing said plunger in a normally open within said stop valve body.

19. A pressure control valve for a handle of an oral irrigation device, said handle comprising:

a valve body having an input section defining an input fluid flow path, an intermediate section having a substantially cylindrical bore therethrough, and a output section defining an output fluid flow path, said input fluid flow path fluidly coupled to said output fluid flow path through said bore;

a valve member positioned in said cylindrical bore and rotatable therein, the valve member having an orifice bored through; and a slide control coupled to the valve member, so that as the slide control moves linearly, the valve member rotates within the bore of the valve body.

20. The pressure control valve of claim 19, wherein as the slide control moves linearly, the valve member rotates within the bore of the valve body between a first position where the orifice is substantially aligned between the input fluid flow path and the output fluid flow path, to a second position where the orifice is substantially mis-aligned between the input fluid flow path and the output fluid flow path.

21. The pressure control valve of claim 19, wherein as the slide control moves linearly, the valve member rotates within the bore of the valve body to alter the effective diameter for fluid flow between the input fluid flow path and the output fluid flow path.

22. The pressure control valve of claim 19, wherein as the slide control moves linearly, the valve member rotates within the bore of the valve body to alter the pressure at which fluid is delivered to the output fluid flow path.

* * * * *